(12) United States Patent
Chen et al.

(10) Patent No.: US 7,879,805 B2
(45) Date of Patent: Feb. 1, 2011

(54) HIGH TEMPERATURE STABLE PEPTIDE FORMULATION

(75) Inventors: Dennis Chen, Milbrae, CA (US); Russell Wayne Blacher, Castro Valley, CA (US); Byeong Chang, Hayward, CA (US)

(73) Assignee: Acologix, Inc., Emeryville, CA (US)

( * ) Notice: Subject to any disclaimer, the term of this patent is extended or adjusted under 35 U.S.C. 154(b) by 293 days.

(21) Appl. No.: 12/129,504

(22) Filed: May 29, 2008

(65) Prior Publication Data

US 2009/0054331 A1  Feb. 26, 2009

Related U.S. Application Data

(60) Provisional application No. 60/941,556, filed on Jun. 1, 2007, provisional application No. 60/969,080, filed on Aug. 30, 2007.

(51) Int. Cl.
*A61K 38/16* (2006.01)
(52) U.S. Cl. .................. 514/21.4; 536/123.13; 424/489
(58) Field of Classification Search ................ 514/21.4; 536/123.13; 424/489
See application file for complete search history.

(56) References Cited

U.S. PATENT DOCUMENTS

| 2003/0202972 | A1* | 10/2003 | Andya et al. ............. 424/131.1 |
| 2004/0105778 | A1 | 6/2004 | Lee et al. |
| 2006/0008415 | A1 | 1/2006 | Kaisheva et al. |
| 2006/0040852 | A1 | 2/2006 | Dix et al. |

FOREIGN PATENT DOCUMENTS

| WO | 99/10011 | 3/1999 |
| WO | 01/49314 | 7/2001 |
| WO | 02/00243 | 1/2002 |
| WO | 03/066666 | 8/2003 |

OTHER PUBLICATIONS

Arakawa et al., "Protein-Solvent Interactions in Pharmaceutical Formulations" Pharmaceutical Research, 8(3):285-291 (1991).
Cleland et al., "The Development of Stable Protein Formulations: A Close Look at Protein Aggregation, Deamidation, and Oxidation" Critical Reviews in Therapeutic Drug Carrier Systems, 10(4):307-377 (1993).
Pikal et al., "Freeze-Drying of Proteins, Part II: Formulation Selection" BioPharm pp. 26-30 (Oct. 1990).
Chen et al., "Influence of Histidine on the Stability and Physical Properties of a Fully Human Antibody in Aqueous and Solid Forms" Pharmaceutical Research, 20(12):1952-62 (Dec. 2003).
Johnson et al., "Mannitol-Sucrose Mixtures—Versatile Formulations for Protein Lyophilization" Journal of Pharmaceutical Sciences, 91:(4)914-922 (Apr. 2002).

\* cited by examiner

*Primary Examiner*—David Lukton
(74) *Attorney, Agent, or Firm*—Karl Bozicevic; Bozicevic, Field & Francis LLP

(57) ABSTRACT

A stabilized pharmaceutical composition in the form of a lyophilized product to be later reconstituted to generate an aqueous drug product is described herein. The therapeutically active ingredient in the form of a peptide of sequence TDLQERGDNDISPFSGDGQPFKD is stabilized with a buffer, carbohydrate stabilizer, a nonionic bulking agent and a surfactant to facilitate reconstitution. The preferred preparation contains a peptide of the sequence TDLQERGDNDIS-PFSGDGQPFKD, histidine buffer, mannitol or glycine, sucrose and/or Polysorbate 20. This combination of excipients has demonstrated exceptional stability as a lyophilized product when stored at the elevated temperature of 40° C. for at least 6 months and for at least 3 Months at 50° C. The lyophilized mixture thus formed is reconstituted to a high peptide concentration without apparent loss of stability of the peptide. Also, this combination of excipients has also enabled the ability to terminally sterilize the lyophilized product using gamma irradiation without affecting the stability of the active ingredient of the formulation.

4 Claims, 1 Drawing Sheet

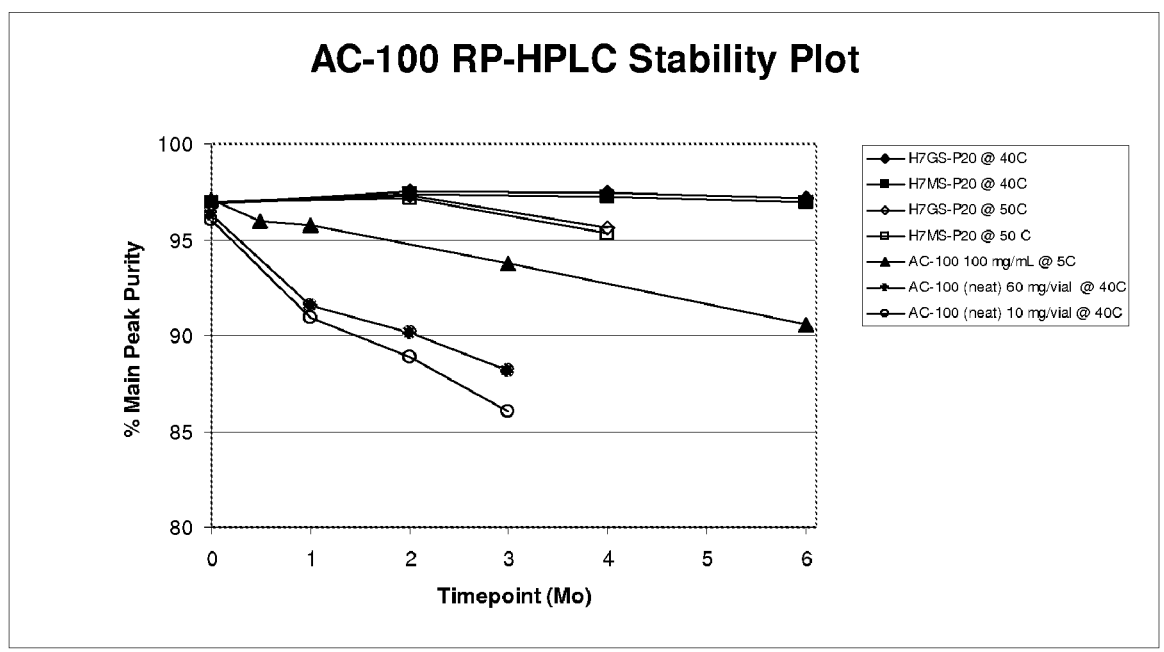
Figure 1. Stability of Various Formulation with AC-100

HIGH TEMPERATURE STABLE PEPTIDE FORMULATION

CROSS-REFERENCE

This application claims the benefit of U.S. Provisional Application Nos. 60/941,556, filed Jun. 1, 2007 and 60/969,080, filed Aug. 30, 2007, which applications are incorporated herein by reference.

TECHNICAL FIELD

The claimed subject matter is directed to a lyophilized peptide formulation. In particular, it relates to a lyophilized peptide formulation that is stable at relatively high temperatures and sterilization by gamma irradiation, which can be reconstituted with a diluent to generate an aqueous drug product which can be administered by injection.

BACKGROUND

Recent advances in biotechnology have made it possible to produce a variety of peptides for pharmaceutical applications using recombinant DNA and synthetic techniques. AC-100, also known as Dentonin®, is a therapeutically active peptide shown to stimulate proliferation, differentiation, and mineralization of human osteoblasts (Nagel et al. (2004) *J. Cell. Biochem.* 93(6):1107-14; U.S. Pat. No. 6,911,425; U.S. Pat. No. 7,078,021 and U.S. Pat. No. 7,160,862). AC-100 has shown bone formation activities in vivo (Hayashibara et al. (2004) *J. Bone and Mineral Res.* 19(3):455-62; Lazarov et al. ((2004) *ASBMR Abs.*); and has also demonstrated stimulation of the proliferation of human dental pulp cells in vitro (Liu et al. (2004) *J. of Dental Res.* 83(6):496-99); as well as formation of new dentin in human dental defects in a clinical trial (Lazarov et al. (2006) *IADR Abs.*).

Accordingly, AC-100 is useful in treating or preventing conditions associated with skeletal loss or weakness, increasing the number and biological activity of osteoblasts, odontoblasts, and other hard tissue forming cells that assist in forming skeletal and dental tissues and promoting regeneration of bones, teeth, and/or cartilage. The described therapeutic peptide may be administered, inter alia, in the treatment of bone defects and breakage, cartilage regeneration, and the stimulation of dental pulp cells to promote hard tissue formation.

Because therapeutic peptides may be larger and more complex than traditional organic and inorganic drugs (i.e., possessing multiple functional groups in addition to possibly complex three-dimensional structures), the formulation of such peptides poses special problems. For a peptide to remain biologically active, a formulation must preserve intact the conformational integrity of at least a core sequence of the peptide's primary structure while at the same time protecting the peptide's multiple functional groups from degradation. Degradation pathways for peptides can involve chemical instability (i.e., any process which involves modification of the peptide by bond formation or cleavage resulting in a new chemical entity) or physical instability (i.e., changes in the higher order structure of the peptide). Chemical instability can result from deamidation, racemization, hydrolysis, oxidation, beta elimination or disulfide exchange. Physical instability can result from denaturation, aggregation, precipitation or adsorption, for example. The three most common peptide degradation pathways are peptide aggregation, deamidation and oxidation. Cleland et al. (1993) *Critical Rev. in Therapeutic Drug Carrier Sys.* 10(4):307-377.

Freeze-drying is a commonly employed technique for preserving peptides which serves to remove water from the peptide preparation of interest. Freeze-drying, or lyophilization, is a process by which the material to be dried is first frozen and then the ice or frozen solvent is removed by sublimation in a vacuum environment. An excipient may be included in pre-lyophilized formulations to enhance stability during the freeze-drying process and/or to improve stability of the lyophilized product upon storage. Pikal, M. (1990) *Biopharm.* 3(9):26-30 and Arakawa et al. (1991) *Pharm. Res.* 8(3):285-291.

It is an object of the present invention to provide a lyophilized peptide formulation, which is stable upon storage and delivery at relatively high temperatures, and which may later be reconstituted to generate an aqueous drug product. It is a further object to provide a stable reconstituted peptide formulation, which is suitable for injectable, such as by intravenous and/or subcutaneous administration, for example. Accordingly, in certain embodiments, it is an object to provide a formulation that is stable as a lyophilized product when stored at elevated temperatures for several months at a time.

Another object of the present invention is to provide a lyophilized peptide formulation, which can be sterilized by radiation. If the peptide in the formulation is susceptible to degradation or structural modification by radiation, the peptide formulation must be sterilized by filtering through sterile filtration membranes prior to, or following, lyophilization and reconstitution. A formulation that enables the terminal sterilization by radiation, e.g., gamma irradiation, would significantly simplify the final sterilization process of the formulated drug.

SUMMARY

The claimed subject matter is based on the discovery that a thermally stable lyophilized peptide formulation can be prepared using a buffer (preferably histidine or phosphate), a lyoprotectant or carbohydrate stabilizer (preferably sucrose), a nonionic bulking agent/tonicity adjuster (preferably mannitol or glycine), and/or a surfactant (preferably Polysorbate 20) to facilitate reconstitution. The lyophilized formulation can be reconstituted to generate a stable reconstituted formulation having a peptide concentration which is significantly higher (e.g., from about 2-80 times higher, preferably 3-20 times higher and most preferably 3-6 times higher) than the peptide concentration in the pre-lyophilized formulation. In particular, while the peptide concentration in the pre-lyophilized formulation may be 10 mg/mL or less, the peptide concentration in the reconstituted formulation is generally 50 mg/mL or more. Such high peptide concentrations in the reconstituted formulation are considered to be particularly useful where the formulation is intended for subcutaneous administration. The lyophilized formulation is stable (i.e., fails to display significant or unacceptable levels of chemical or physical instability of the peptide) at 40° C. for at least about 6 months and is stable at 50° C. for at least about 3 months. Peptides, such as AC-100, in the lyophilized formulation essentially retain their physical and chemical stability and integrity upon lyophilization and storage. In certain embodiments, the reconstituted formulation is isotonic.

When reconstituted with a diluent comprising a preservative (such as bacteriostatic water for injection ("BWFI")), the reconstituted formulation may be used as a multi-use formulation. Such a formulation is useful, for example, where the patient requires frequent subcutaneous administrations of the peptide to treat a chronic medical condition. The advantage of a multi-use formulation is that it facilitates ease of use for the patient, reduces waste by allowing complete use of vial contents, and results in a significant cost savings for the manufacturer since several doses are packaged in a single vial (lower filling and shipping costs).

The ratio of lyoprotectant:peptide in the lyophilized formulation of the preceding paragraphs depends, for example, on both the peptide and lyoprotectant of choice, as well as the desired peptide concentration and isotonicity of the reconstituted formulation. In the case of AC-100 (as the peptide of SEQ ID NO: 1) and sucrose (as the lyoprotectant) for generating a high peptide concentration isotonic reconstituted formulation, the ratio may, for example, be about 10-100 moles of sucrose: 1 mole AC-100±20%.

Generally, the pre-lyophilized formulation of the peptide and lyoprotectant will further include a buffer which provides the formulation at a suitable pH. For this purpose, it has been found to be desirable to use a histidine buffer in that, as demonstrated below, this appears to have lyoprotective properties.

The formulation may further include a surfactant (e.g., a polysorbate) in that it has been observed herein that this can reduce aggregation of the reconstituted peptide and/or reduce the formation of particulates in the reconstituted formulation. The surfactant can be added to the pre-lyophilized formulation, the lyophilized formulation and/or the reconstituted formulation (but preferably the pre-lyophilized formulation) as desired.

In yet a further embodiment, the invention provides a method for preparing a formulation comprising the steps of: (a) lyophilizing a mixture of a peptide and a lyoprotectant; and (b) reconstituting the lyophilized mixture of step (a) in a diluent such that the reconstituted formulation is isotonic and has a peptide concentration of at least about 5 mg/mL. For example, the peptide concentration in the reconstituted formulation may be from about 10 mg/mL to about 400 mg/mL. Generally, the peptide concentration in the reconstituted formulation is about 2-80 times greater than the peptide concentration in the mixture before lyophilization with all numbers being ±20%.

An article of manufacture is also provided herein which comprises: (a) a container which holds a lyophilized mixture of the peptide and a lyoprotectant; and (b) instructions for reconstituting the lyophilized mixture with a diluent to a peptide concentration in the reconstituted formulation of at least about 50 mg/mL. The article of manufacture may further comprise a second container which holds a diluent (e.g., WFI or BWFI comprising an aromatic alcohol).

The invention further provides a method for treating a mammal comprising administering a therapeutically effective amount of the reconstituted formulation disclosed herein to a mammal, wherein the mammal has a disorder requiring treatment with the peptide in the formulation. For example, the formulation may be administered intravenously or subcutaneously.

One useful peptide pre-lyophilized formulation as discovered in the experiment detailed below was found to comprise AC-100 in an amount from about 5-40 mg/mL (e.g., 20-30 mg/mL) and sucrose in an amount from about 10-100 mM (e.g., 40-80 mM) with all numbers being ±20%, glycine from about 50-250 (e.g., 75-150 mM) mM with all numbers being ±20%, a buffer (e.g., histidine, pH 7) and a surfactant (e.g., a polysorbate). The lyophilized formulation was found to be stable at 40° C. for at least 6 months and stable at 50° C. for at least 3 months. This peptide formulation can be reconstituted with a diluent to generate a formulation suitable for intravenous and/or subcutaneous administration comprising AC-100 in an amount of about 10-30 mg/mL. Where higher concentrations of the peptide are desired (for example, where subcutaneous delivery of the peptide is the intended mode of administration to the patient), the lyophilized formulation may be reconstituted to yield a reconstituted formulation having a peptide concentration of 50 mg/mL or more.

The invention includes a formulation comprised of a peptide which peptide may be any one of the sequences of the SEQ ID NOS:1-10 shown here. The formulation will include a buffer which may be histidine and a carbohydrate stabilize which may be sucrose along with a bulking agent such as glycine and surfactant such as Polysorbate 20.

The formulation of the invention may be a lyophilized mixture which is comprised of a non-reducing sugar such as sucrose, a peptide such as the peptide of any of the sequences of SEQ ID NO:1-10, a bulking agent such as glycine and a buffer such as histidine wherein the molar ratio of the non-reducing sugar to the peptide is within a range of from about 20 to 200 moles of non-reducing sugar to 1 mole of peptide with the ratio being an approximation ±20%.

The invention also includes a sterile reconstituted formulation which includes the lyophilized mixture as described above reconstituted using a diluent such as sterile water or bacteriostatic water which diluent may be isotonic. The resulting reconstituted formulation includes the peptide in an amount in the range of from about 1 mg/ml to about 300 mg/ml ±20%. The lyophilized mixture may be reconstituted using a pH buffered solution, a sterile saline solution, Ringer's solution and a dextrose solution.

The invention can further include a manufactured article which includes the reconstituted formulation described above along with instructions for reconstituting the lyophilized mixture with a diluent to provide a formulation having the peptide concentrations as described here.

These and other objects, advantages, and features of the invention will become apparent to those persons skilled in the art upon reading the details of the subject invention, as more fully described below.

BRIEF DESCRIPTION OF THE DRAWINGS

The invention is best understood from the following detailed description when read in conjunction with the accompanying drawings. It is emphasized that, according to common practice, the various features of the drawings are not-to-scale. On the contrary, the dimensions of the various features are arbitrarily expanded or reduced for clarity. Included in the drawings are the following figures:

FIG. 1 illustrates the increase in stability of AC-100 lyophilized formulation. The formulations H7GS-P20 (histidine pH 7/glycine/sucrose/Tween 20) and H7MS-P20 (histidine pH 7/mannitol/sucrose/Tween 20). The lyophilized cake was incubated at 40° C. for 6 mo or 40° C. for 3 weeks followed by and additional 3 Mo at 50° C. (Noted as 50° C.), then reconstituted. The fraction of intact peptide in the reconstituted formulation was measured by reversed-phase chromatography and defined as the peak area of the native peptide relative to the total peak area including degradants. This is compared to lyophilized AC-100 sans excipients (neat) stored at 40° C. and the current liquid formulation of AC-100 100 mg/mL (90 mM NaCl, pH 7) stored at the accelerated stability condition of 5° C.

BRIEF DESCRIPTION OF THE SEQUENCES

SEQ ID NO: 1 is set forth as TDLQERGDNDISPFS-GDGQPFKD, which corresponds to the amino acid sequence of the therapeutically active ingredient of the invention, AC-100. AC-100 was identified as a small fragment within a large molecule referred to as matrix extracellular phosphoglycoprotein ("MEPE"). AC-100 is characterized by a few unique motifs, such as an RGD integrin-binding motif, and a SGDG glycosaminoglycan motif. These motifs are believed to give the molecule an essential structure resulting in its bioactivity which is preserved over a longer period of time using a formulation of the invention.

SEQ ID NO:2 is set forth as TDLQEDGRNDISPFS-GDGQPFKD, which corresponds to the amino acid sequence of the therapeutically active ingredient of the invention, AC-101. This is a mutant of AC-100 where the RGD integrin-binding motif was scrambled. The RGD sequence was changed to DGR.

SEQ ID NO:3 is set forth as TDLQERGDNDISPFGDG-SQPFKD, which corresponds to the amino acid sequence of the therapeutically active ingredient of the invention, AC-102. This is a mutant of AC-100 where the SGDG glycosaminoglycan motif was scrambled. The SGDG sequence was changed to GDGS.

SEQ ID NO:4 is set forth as TDLQEDGRNDISPFGDG-SQPFKD, which corresponds to the amino acid sequence of the therapeutically active ingredient of the invention, AC-103. This is a double-mutant of AC-100 where both the integrin-binding and glycosaminoglycan motifs have been modified. The integrin-binding motif sequence was changed from RGD and substituted with DGR and the glycosaminoglycan motif sequence was changed from SGDG to GDGS.

SEQ ID NO:5 is set forth as TDLQEDRGNDISPFS-GDGQPFKD. This is a mutant of AC-100 where the RGD integrin-binding motif was scrambled. The RGD sequence was changed to DRG.

SEQ ID NO:6 is set forth as TDLQERWDNDISPFS-GDGQPFKD.

SEQ ID NO:7 is set forth as TDLQERGDNDMSPFS-GDGQPFKD.

SEQ ID NO:8 is set forth as PDLQERGDNDISPFS-GDGQPFKD.

SEQ ID NO:9 is set forth as PDLQGRGDNDLSPFSGDG-PPFKD.

SEQ ID NO:10 is set forth as PDLLVRGDNDVPPFS-GDGQHFMH.

All of the sequences in this invention are amidated at their C-terminal.

DETAILED DESCRIPTION OF THE PREFERRED EMBODIMENTS

Before the mixtures, methods, peptides, analogs, and formulations including reconstituted formulations of the present invention are described, it is to be understood that this invention is not limited to any particular embodiment described, as such may, of course, vary. It is also to be understood that the terminology used herein is with the purpose of describing particular embodiments only, and is not intended to limit the scope of the present invention which will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited. The present disclosure is controlling to the extent there is a contradiction between the present disclosure and a publication incorporated by reference.

It must be noted that as used herein and in the appended claims, the singular forms "a", "and", and "the" include plural referents unless the context clearly dictates otherwise. Thus, for example, reference to "a peptide" includes a plurality of such peptides and reference to "the method" includes reference to one or more methods and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

By "protein" is meant a sequence of amino acids for which the chain length is sufficient to produce the higher levels of tertiary and/or quaternary structure. This is to distinguish from "peptides" or other small molecular weight drugs that do not have such structure. Typically, a protein will have a molecular weight of about 15-20 kD to about 20 kD.

The terms "peptide" and "peptidic compound" are used interchangeably herein to refer to a polymeric form of amino acids of from about 10 to about 50 amino acids (may consist of at least 10 and not more than 50 amino acids), which can comprise coded and non-coded amino acids, chemically or biochemically modified or derivatized amino acids, L- or D-amino acids, peptides having modified peptide backbones, and peptides comprising amino acid analogs. The amino acid may be limited to only amino acids naturally occurring in humans. The peptidic compounds may be polymers of: (a) naturally occurring amino acid residues; (b) non-naturally occurring amino acid residues, e.g., N-substituted glycines, amino acid substitutes, etc.; or (c) both naturally occurring and non-naturally occurring amino acid residues/substitutes. In other words, the subject peptidic compounds may be peptides or peptoids. Peptoid compounds and methods for their preparation are described in WO 91/19735, the disclosure of which is hereby incorporated in its entirety by reference herein. A peptide compound of the invention may comprise or consist of 23 amino acids or from 18 to 28 amino acids or from 20 to 26 amino acids. The active amino acid sequence of the invention comprises or consists of two characteristic motifs which may be overlapping, which are: an integrin binding motif sequence and a glycosaminoglycan binding motif sequence.

The terms "treatment", "treating" and the like are used herein to refer to both therapeutic treatment and prophylactic or preventative measures. Those in need of treatment include those already with the disorder as well as those in which the disorder is to be prevented. In general, this encompasses obtaining a desired pharmacologic and/or physiologic effect, e.g., stimulation of angiogenesis. The effect may be prophylactic in terms of completely or partially preventing a disease or symptom thereof and/or may be therapeutic in terms of a partial or complete cure for a disease and/or adverse effect attributable to the disease. The terms as used herein cover any treatment of a disease in a mammal, particularly a human, and include: (a) preventing a disease or condition (e.g., preventing the loss of cartilage) from occurring in a subject who may be predisposed to the disease but has not yet been diagnosed as having it; (b) inhibiting the disease, e.g., arresting loss of cartilage; or (c) relieving the disease (e.g., enhancing the development of cartilage).

The terms "subject," "individual," "patient," and "host" are used interchangeably herein and refer to any vertebrate, particularly any mammal and most particularly including human subjects, farm animals, and mammalian pets. The subject may be, but is not necessarily under the care of a health care professional such as a doctor.

The peptide which is formulated is preferably essentially pure and desirably essentially homogeneous (i.e., free from contaminating peptides, etc.). "Essentially pure" peptide means a composition comprising at least about 90% by weight of the peptide, based on total weight of the composition, and preferably at least about 95% by weight. "Essentially homogeneous" peptide means a composition comprising at least about 99% by weight of peptide, based on total weight of the composition.

A "stable" formulation is one in which the peptide therein essentially retains its physical and chemical stability and integrity upon storage and exposure to relatively high temperatures. Various analytical techniques for measuring peptide stability are available in the art and are reviewed in *Peptide and Protein Drug Delivery*, 247-301, Vincent Lee Ed., Marcel Dekker, Inc., New York, N.Y., Pubs. (1991), and Jones, A. (1993) *Adv. Drug Delivery Rev.* 10:29-90. Stability can be measured at a selected temperature for a selected time period. For rapid screening, the formulation may be kept at 40° C. for 2 weeks to 1 month, at which time stability is measured. Where the formulation is to be stored at 2-8° C., generally the formulation should be stable at 30° C. or 40° C. for at least 1 month and/or stable at 2-8° C. for at least 2 years. Where the formulation is to be stored at 30° C., generally the formulation should be stable for at least 2 years at 30° C. and/or stable at 40° C. for at least 6 months. For example, the extent of aggregation following lyophilization and storage can be used as an indicator of peptide stability. For example, a "stable" formulation may be one wherein less than about 10% and preferably less than about 5% of the peptide is present as an aggregate in the formulation. In other embodiments, any increase in aggregate formation following lyophilization and storage of the lyophilized formulation can be determined. For example, a "stable" lyophilized formulation may be one wherein the increase in aggregate in the lyophilized formulation is less than about 5% and preferably less than about 3%, when the lyophilized formulation is stored at 2-8° C. for at least one year. In other embodiments, stability of the peptide formulation may be measured using a biological activity assay (see, e.g., Example 1).

A "reconstituted" formulation is one which has been prepared by dissolving a lyophilized peptide formulation in a diluent such that the peptide is dispersed in the reconstituted formulation. The reconstituted formulation is suitable for administration (e.g. parenteral administration) to a patient to be treated with the peptide of interest and, in certain embodiments of the invention, may be one which is suitable for subcutaneous administration.

By "isotonic" is meant that the formulation of interest has essentially the same osmotic pressure as human blood. Isotonic formulations will generally have an osmotic pressure from about 250 to 350 mOsm (one-thousandth of an osmole, which is a non-SI unit of measurement that defines the number of moles of a chemical compound that contribute to a solution's osmotic pressure). Isotonicity can be measured using a vapor pressure or ice-freezing type osmometer, for example.

A "lyoprotectant" is a molecule which, when combined with a peptide of interest, significantly prevents or reduces chemical and/or physical instability of the peptide upon lyophilization and subsequent storage. Exemplary lyoprotectants include sugars such as sucrose or trehalose; an amino acid such as monosodium glutamate or histidine; a methylamine such as betaine; a lyotropic salt such as magnesium sulfate; a polyol such as trihydric or higher sugar alcohols, e.g., glycerin, erythritol, glycerol, arabitol, xylitol, sorbitol, and mannitol; propylene glycol; polyethylene glycol; Pluronics; and combinations thereof. The preferred lyoprotectant is a non-reducing sugar, such as trehalose or sucrose.

The lyoprotectant is added to the pre-lyophilized formulation in a "lyoprotecting amount" which means that, following lyophilization of the peptide in the presence of the lyoprotecting amount of the lyoprotectant, the peptide essentially retains its physical and chemical stability and integrity upon lyophilization and storage.

The "diluent" of interest herein is one which is pharmaceutically acceptable (safe and non-toxic for administration to a human) and is useful for the preparation of a reconstituted formulation. Exemplary diluents include sterile water, sterile water for injection (WFI), bacteriostatic water for injection ("BWFI"), a pH buffered solution (e.g., phosphate-buffered saline), sterile saline solution, Ringer's solution or dextrose solution.

A "preservative" is a compound which can be added to the diluent to essentially reduce bacterial action in the reconstituted formulation, thus facilitating the production of a multi-use reconstituted formulation, for example. Examples of potential preservatives include octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride. Other types of preservatives include aromatic alcohols such as phenol, butyl and benzyl alcohol, alkyl parabens such as methyl or propyl paraben, catechol, resorcinol, cyclohexanol, 3-pentanol, and m-cresol. The most preferred preservative herein is benzyl alcohol.

A "bulking agent" is a compound which adds mass to the lyophilized mixture and contributes to the physical structure of the lyophilized cake (e.g., facilitates the production of an essentially uniform lyophilized cake which maintains an open pore structure). Exemplary bulking agents include mannitol, glycine and polyethylene glycol.

"Mammal" for purposes of treatment refers to any animal classified as a mammal, including humans, domestic and farm animals, and zoo, sports, or pet animals, such as dogs, horses, cats, cows, etc. Preferably, the mammal is human.

A "disorder" is any condition that would benefit from treatment with the peptide. This includes chronic and acute disorders or diseases including those pathological conditions which predispose the mammal to the disorder in question. Non-limiting examples of disorders to be treated herein include skeletal loss or weakness and bone defects or breakage.

"Terminal Sterilization" by Radiation a process for sterilization of drug product using radiation, preferably gamma irradiation

MODES FOR CARRYING OUT THE INVENTION

A. Peptide Preparation

The peptide to be formulated is prepared using techniques which are well established in the art including synthetic techniques (such as recombinant techniques and peptide synthesis or a combination of these techniques) or may be isolated from an endogenous source of the peptide.

B. Preparation of the Lyophilized Formulation

After preparation of the peptide of interest as described above, a "pre-lyophilized formulation" is produced. The amount of peptide present in the pre-lyophilized formulation is determined taking into account the desired dose volumes, mode(s) of administration, etc. The peptide is generally present in solution. For example, the peptide may be present in a pH-buffered solution at a pH from about 4-8, and preferably from about 5-7. Exemplary buffers include histidine, phosphate, acetate, Tris, citrate, succinate and other organic acids. The buffer concentration can be from about 1 mM to about 20 mM, or from about 3 mM to about 15 mM, depending, for example, on the buffer and the desired tonicity of the formulation (e.g., of the reconstituted formulation). The preferred buffer is histidine in that, as demonstrated below, this can have lyoprotective properties.

The lyoprotectant is added to the pre-lyophilized formulation. In preferred embodiments, the lyoprotectant is a non-reducing sugar such as sucrose or trehalose. The amount of lyoprotectant in the pre-lyophilized formulation is generally such that, upon reconstitution, the resulting formulation will be isotonic. However, hypertonic reconstituted formulations may also be suitable. In addition, the amount of lyoprotectant must not be too low such that an unacceptable amount of degradation/aggregation of the peptide occurs upon lyophilization. Where the lyoprotectant is a sugar (such as sucrose or trehalose) and the peptide is AC-100, exemplary lyoprotectant concentrations in the pre-lyophilized formulation are from about 5 mM to about 400 mM, and preferably from about 10 mM to about 200 mM, and most preferably from about 20 mM to about 100 mM.

The ratio of peptide to lyoprotectant may be selected depending on the peptide and lyoprotectant combination. In the case of AC-100 as the peptide of choice and a sugar (e.g., sucrose or trehalose) as the lyoprotectant for generating an isotonic reconstituted formulation with a high peptide concentration, the molar ratio of lyoprotectant to AC-100 may be from about 10 to about 1500 moles lyoprotectant to 1 mole AC-100, and preferably from about 20 to about 1000 moles of lyoprotectant to 1 mole AC-100, for example from about 200 to about 600 moles of lyoprotectant to 1 mole AC-100.

In preferred embodiments of the invention, it has been found to be desirable to add a surfactant to the pre-lyophilized formulation. Alternatively, or in addition, the surfactant may be added to the lyophilized formulation and/or the reconstituted formulation. Exemplary surfactants include nonionic surfactants such as polysorbates (e.g., polysorbates 20 or 80); poloxamers (e.g., poloxamer 188); Triton; sodium dodecyl sulfate (SDS); sodium laurel sulfate; sodium octyl glycoside; lauryl-, myristyl-, linoleyl-, or stearyl-sulfobetaine; lauryl-, myristyl-, linoleyl- or stearyl-sarcosine; linoleyl-, myristyl-, or cetyl-betaine; lauroamidopropyl-, cocamidopropyl-, linoleamidopropyl-, myristamidopropyl-, palmidopropyl-, or isostearamidopropyl-betaine (e.g., lauroamidopropyl); myristamidopropyl-, palmidopropyl-, or isostearamidopropyl-dimethylamine; sodium methyl cocoyl-, or disodium methyl oleyl-taurate; and the MONAQUAT™ series (Mona Industries, Inc., Paterson, N.J.), polyethyl glycol, polypropyl glycol, and copolymers of ethylene and propylene glycol (e.g., Pluronics, PF68 etc). The amount of surfactant added is such that it reduces aggregation of the reconstituted peptide and minimizes the formation of particulates after reconstitution. For example, the surfactant may be present in the pre-lyophilized formulation in an amount from about 0.001-0.5%, and preferably from about 0.005-0.05%.

In certain embodiments of the invention, a mixture of the lyoprotectant (such as sucrose or trehalose) and a bulking agent (e.g., mannitol or glycine) is used in the preparation of the pre-lyophilization formulation. The bulking agent may allow for the production of a uniform lyophilized cake without excessive pockets therein, etc.

Other pharmaceutically acceptable carriers, excipients or stabilizers such as those described in Remington's Pharmaceutical Sciences 16th edition, Osol, A. Ed. (1980) may be included in the pre-lyophilized formulation (and/or the lyophilized formulation and/or the reconstituted formulation) provided that they do not adversely affect the desired characteristics of the formulation. Acceptable carriers, excipients or stabilizers are nontoxic to recipients at the dosages and concentrations employed and include additional buffering agents; preservatives; co-solvents; antioxidants including ascorbic acid and methionine; chelating agents such as EDTA; metal complexes (e.g., Zn-peptide complexes); biodegradable polymers such as polyesters; and/or salt-forming counter-ions such as sodium.

The formulation herein may also contain more than one peptide as necessary for the particular indication being treated, preferably those with complementary activities that do not adversely affect the other peptide. Such peptides are suitably present in combination in amounts that are effective for the purpose intended.

The formulations to be used for in vivo administration must be sterile. This is readily accomplished by filtration through sterile filtration membranes, prior to, or following, lyophilization and reconstitution. Alternatively, sterility of the entire mixture may be accomplished by autoclaving the ingredients, except for the peptide, at about 120° C. for about 30 minutes, for example. Alternatively, terminal sterilization by radiation of the entire mixture prior to reconstitution may be accomplished by gamma irradiation of the lyophilized product.

After the peptide, lyoprotectant and other optional components are mixed together, the formulation is lyophilized. Many different freeze-dryers are available for this purpose such as Hull50™ (Hull, USA) or GT20™ (Leybold-Heraeus, Germany) freeze-dryers. Freeze-drying is accomplished by freezing the formulation and subsequently subliming ice from the frozen content at a temperature suitable for primary drying. Under this condition, the product temperature is below the eutectic point or the collapse temperature of the formulation. Typically, the shelf temperature for the primary drying will range from about −30 to 25° C. (provided the product remains frozen during primary drying) at a suitable pressure, ranging typically from about 50 to 250 mTorr. The formulation, size and type of the container holding the sample (e.g., glass vial) and the volume of liquid will mainly dictate the time required for drying, which can range from a few hours to several days (e.g., 40-60 hours). A secondary drying stage may be carried out at about −15-40° C., depending primarily on the type and size of container and the type of peptide employed. Or, the shelf temperature throughout the entire water removal phase of lyophilization may be from about 15-30° C. (e.g., about 25° C.). The time and pressure required for secondary drying will be that which produces a suitable lyophilized cake, dependent, e.g., on the temperature and other parameters. The secondary drying time is dictated by the desired residual moisture level in the product and typically takes at least about 5 hours (e.g., 10-15 hours). The pressure may be the same as that employed during the primary drying step. Freeze-drying conditions can be varied depending on the formulation and vial size.

In some instances, it may be desirable to lyophilize the peptide formulation in the container in which reconstitution of the peptide is to be carried out in order to avoid a transfer step. The container in this instance may, for example, be a 1, 2, 3, 5, 10, 20, 50 or 100 cc vial.

As a general proposition, lyophilization will result in a lyophilized formulation in which the moisture content thereof is less than about 5%, and preferably less than about 2% and most preferably less than about 1%

C. Reconstitution of the Lyophilized Formulation

At the desired stage, typically when it is time to administer the peptide to the patient, the lyophilized formulation may be reconstituted with a diluent such that the peptide concentration in the reconstituted formulation is at least 50 mg/mL, for example from about 50 mg/mL to about 400 mg/mL, more preferably from about 80 mg/mL to about 300 mg/mL, and most preferably from about 90 mg/mL to about 150 mg/mL. Such high peptide concentrations in the reconstituted formulation are considered to be particularly useful where subcutaneous delivery of the reconstituted formulation is intended. However, for other routes of administration, such as intravenous administration, lower concentrations of the peptide in the reconstituted formulation may be desired (for example from about 5-50 mg/mL, or from about 10-40 mg/mL peptide in the reconstituted formulation). In certain embodiments, the peptide concentration in the reconstituted formulation is significantly higher than that in the pre-lyophilized formulation. For example, the peptide concentration in the reconstituted formulation may be about 2-40 times, preferably 3-10 times and most preferably 3-6 times (e.g., at least three fold or at least four fold) that of the pre-lyophilized formulation.

Reconstitution generally takes place at a temperature of about 25° C. to ensure complete hydration, although other temperatures may be employed as desired. The time required for reconstitution will depend, e.g., on the type of diluent, amount of excipient(s) and peptide. Exemplary diluents include sterile water, sterile water for injection (WFI), bacteriostatic water for injection (BWFI), a pH buffered solution (e.g., phosphate-buffered saline), sterile saline solution, Ringer's solution or dextrose solution. The diluent optionally contains a preservative. Exemplary preservatives have been described above, with aromatic alcohols such as benzyl alcohol or phenol being the preferred preservatives. The amount of preservative employed is determined by assessing different preservative concentrations for compatibility with the peptide and preservative efficacy testing. For example, if the preservative is an aromatic alcohol (such as benzyl alcohol), it can be present in an amount from about 0.1-2.0% and preferably from about 0.5-1.5%, but most preferably about 1.0-1.2%.

Preferably, the reconstituted formulation has less than 6000 particles per vial which are ≧10 μm in size.

D. Administration of the Reconstituted Formulation

The reconstituted formulation is administered to a mammal in need of treatment with the peptide, preferably a human, in accord with known methods, such as intravenous administration as a bolus or by continuous infusion over a period of time, by intramuscular, intraperitoneal, intracerobrospinal, subcutaneous, intra-articular, intrasynovial, intrathecal, oral, topical, or inhalation routes.

The formulation of may be administered to the individual using any available method and route suitable for drug delivery, including in vivo and ex vivo methods, as well as systemic and localized routes of administration.

Conventional and pharmaceutically acceptable routes of administration include intranasal, intrapulmonary, intramuscular, intratracheal, subcutaneous, intradermal, intra-articular, topical application, intravenous, rectal, nasal, oral and other parenteral routes of administration. Routes of administration may be combined, if desired, or adjusted depending upon the immunomodulatory nucleic acid molecule and/or the desired effect on the immune response. The peptidic compound formulation for use with the methods of the present invention can be administered in a single dose or in multiple doses.

The peptidic compound formulation can be administered to a subject using any available conventional methods and routes suitable for delivery of conventional drugs, including systemic or localized routes. In general, routes of administration contemplated by the invention include, but are not necessarily limited to, enteral, parenteral, implantable, or inhalational routes.

Parenteral routes of administration other than inhalation administration include, but are not necessarily limited to, topical, transdermal, subcutaneous, intramuscular, intraorbital, intracapsular, intraspinal, intrasternal, intra-articular, and intravenous routes, i.e., any route of administration other than through the alimentary canal. Parenteral administration can be carried to effect systemic or local delivery of peptides of the invention. Where systemic delivery is desired, administration typically involves invasive or systemically absorbed topical or mucosal administration of pharmaceutical preparations.

The peptidic compound formulation of the invention can also be delivered to the subject by enteral administration. Enteral routes of administration include, but are not necessarily limited to, oral and rectal (e.g., using a suppository) delivery.

Methods of administration of the peptidic compound formulation through the skin or mucosa include, but are not necessarily limited to, topical application of a suitable pharmaceutical preparation with or without a permeation enhancer, transdermal transmission, injection and epidermal administration. Also contemplated for delivery of the peptidic compound formulation of the invention is a patch containing therein a peptide of the invention. A patch can be applied to the skin, or to other tissue, e.g., gum tissue. Any known patch delivery system that is suitable for oral delivery system can be used. See, e.g., U.S. Pat. No. 6,146,655.

In preferred embodiments, the reconstituted formulation is administered to the mammal by subcutaneous (i.e., beneath the skin) administration. For such purposes, the formulation may be injected using a syringe. However, other devices for administration of the formulation are available such as injection devices (e.g., the Inject-ease™ and Genject™ devices);

injector pens (such as the GenPen™); needleless devices (e.g., MediJector™ and BioJector™); and subcutaneous patch delivery systems.

The appropriate dosage ("therapeutically effective amount") of the peptide will depend, for example, on the condition to be treated, the severity and course of the condition, whether the peptide is administered for preventive or therapeutic purposes, previous therapy, the patient's clinical history and response to the peptide, the type of peptide used, and the discretion of the attending physician. The peptide is suitably administered to the patient at one time or over a series of treatments and may be administered to the patient at any time from diagnosis onwards. The peptide may be administered as the sole treatment or in conjunction with other drugs or therapies useful in treating the condition in question. The progress of this therapy is easily monitored by conventional techniques. Exemplary dosages of AC-100 are in the range 1-50 mg/kg by one or more separate administrations.

E. Articles of Manufacture

In another embodiment of the invention, an article of manufacture is provided which contains the lyophilized formulation of the present invention and provides instructions for its reconstitution and/or use. The article of manufacture comprises a container. Suitable containers include, for example, bottles, vials (e.g., dual chamber vials), syringes (such as dual chamber syringes) and test tubes. The container may be formed from a variety of materials such as glass or plastic. The container holds the lyophilized formulation and the label on, or associated with, the container may indicate directions for reconstitution and/or use. For example, the label may indicate that the lyophilized formulation is reconstituted to peptide concentrations as described above. The label may further indicate that the formulation is useful or intended for subcutaneous administration. The container holding the formulation may be a multi-use vial, which allows for repeat administrations (e.g., from 2-6 administrations) of the reconstituted formulation. The article of manufacture may further comprise a second container comprising a suitable diluent (e.g., BWFI). Upon mixing of the diluent and the lyophilized formulation, the final peptide concentration in the reconstituted formulation will generally be at least 50 mg/mL. The article of manufacture may further include other materials desirable from a commercial and user standpoint, including other buffers, diluents, filters, needles, syringes, and package inserts with instructions for use.

The invention will be more fully understood by reference to the following examples. They should not, however, be construed as limiting the scope of the invention. All literature citations are incorporated by reference.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1

A. AC-100 (SEQ ID NO:1) Formulation

In the development of a lyophilized formulation, excipients and buffers are initially screened by measuring the stability of the peptide after lyophilization and reconstitution. The lyophilized peptide in each formulation is also subjected to accelerated stability studies to determine the potential stability of the peptide over its shelf-life.

In early screening studies, the stability of several lyophilized AC-100 formulations may be investigated after incubation at 5° C. (proposed storage condition) and 40° C. (accelerated stability condition).

The stabilizing effects of various lyoprotectant sugars on the lyophilized peptide may be measured.

The delivery of a high peptide concentration is often required for subcutaneous administration due to the volume limitations ($\leq 1.5$ mL) and dosing requirements ($\geq 100$ mg). However, high peptide concentrations ($\geq 50$ mg/mL) are often difficult to achieve in the manufacturing process since at high concentrations, the peptide has a tendency to aggregate and/or degrade during processing and becomes difficult to manipulate (e.g., pump) and sterile filter. Alternatively, the lyophilization process may provide a method to allow concentration of the peptide. For example, the peptide is filled into vials at a volume (Vf) and then lyophilized. The lyophilized peptide is then reconstituted with a smaller volume (Vr) of water or preservative (e.g., BWFI) than the original volume (e.g., Vr=0.25 Vf) resulting in a higher peptide concentration in the reconstituted solution. This process also results in the concentration of the buffers and excipients. For subcutaneous administration, the solution is desirably isotonic.

For subcutaneous administration, the formulation was reconstituted to 50 mg/mL (0.2 mL WFI). At this high peptide concentration, the peptide may be more susceptible to aggregation than an intravenous dosage reconstituted to 22 mg/mL peptide (2.2 mL BWFI). This unconstituted formulation maintained the peptide completely intact at the elevated temperature of 40° C. for at least 6 months and at the elevated temperature of 50° C. for at least 3 months, indicating that the lyophilized peptide could be stored at relatively high temperatures.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of the present invention is embodied by the appended claims.

The invention claimed is:

1. A lyophilized mixture, comprising:
   a non-reducing sugar;
   a peptide;
   a bulking agent; and
   histidine;
   wherein the molar ratio of the non-reducing sugar to the peptide is within a range from 20 to 200 moles of non-reducing sugar:1 mole peptide±20%;
   wherein the peptide is selected from the group consisting of:

```
TDLQERGDNDISPFSGDGQPFKD       (SEQ ID NO:1)

TDLQEDGRNDISPFSGDGQPFKD       (SEQ ID NO:2)

TDLQERGDNDISPFGDGSQPFKD       (SEQ ID NO:3)

TDLQEDGRNDISPFGDGSQPFKD       (SEQ ID NO:4)

TDLQEDRGNDISPFSGDGQPFKD       (SEQ ID NO:5)

TDLQERWDNDISPFSGDGQPFKD       (SEQ ID NO:6)

TDLQERGDNDMSPFSGDGQPFKD       (SEQ ID NO:7)

PDLQERGDNDISPFSGDGQPFKD       (SEQ ID NO:8)

PDLQGRGDNDLSPFSGDGPPFKD;      (SEQ ID NO:9)

and

PDLLVRGDNDVPPFSGDGQHFMH.      (SEQ ID NO:10)
```

2. The lyophilized mixture of claim 1, wherein the nonreducing sugar is sucrose and the molar ratio of sucrose to peptide is within the range from 20 to 100 moles sucrose:1 mole peptide±20%.

3. The lyophilized mixture of claim 1, wherein any increase in aggregated or degraded peptide in the lyophilized formulation is less than about 5% when the lyophilized formulation is stored at a condition selected from the group consisting of 25° C. for at least one year, 40° C. for at least 6 months and 50° C. for at least 4 months.

4. The lyophilized mixture of claim 1, characterized by a moisture content of less than 1.5% and being terminally sterilized via gamma irradiation.

* * * * *

SEQUENCE LISTING

<160> NUMBER OF SEQ ID NOS: 10

<210> SEQ ID NO 1
<211> LENGTH: 23
<212> TYPE: PRT
<213> ORGANISM: Artificial Sequence
<220> FEATURE:
<223> OTHER INFORMATION: synthetic peptide

<400> SEQUENCE: 1

Thr Asp Leu Gln Glu Arg Gly Asp Asn Asp Ile Ser Pro Phe Ser Gly
 1               5                  10                  15

Asp Gly Gln Pro Phe Lys Asp
            20

<210> SEQ ID NO 2
<211> LENGTH: 23
<212> TYPE: PRT
<213> ORGANISM: Artificial Sequence
<220> FEATURE:
<223> OTHER INFORMATION: synthetic peptide

<400> SEQUENCE: 2

Thr Asp Leu Gln Glu Asp Gly Arg Asn Asp Ile Ser Pro Phe Ser Gly
 1               5                  10                  15

Asp Gly Gln Pro Phe Lys Asp
            20

<210> SEQ ID NO 3
<211> LENGTH: 23
<212> TYPE: PRT
<213> ORGANISM: Artificial Sequence
<220> FEATURE:
<223> OTHER INFORMATION: synthetic peptide

<400> SEQUENCE: 3

Thr Asp Leu Gln Glu Arg Gly Asp Asn Asp Ile Ser Pro Phe Gly Asp
 1               5                  10                  15

Gly Ser Gln Pro Phe Lys Asp
            20

<210> SEQ ID NO 4
<211> LENGTH: 23
<212> TYPE: PRT
<213> ORGANISM: Artificial Sequence
<220> FEATURE:
<223> OTHER INFORMATION: synthetic peptide

<400> SEQUENCE: 4

Thr Asp Leu Gln Glu Asp Gly Arg Asn Asp Ile Ser Pro Phe Gly Asp
 1               5                  10                  15

Gly Ser Gln Pro Phe Lys Asp
            20

<210> SEQ ID NO 5
<211> LENGTH: 23
<212> TYPE: PRT
<213> ORGANISM: Artificial Sequence
<220> FEATURE:
<223> OTHER INFORMATION: synthetic peptide

<400> SEQUENCE: 5

Thr Asp Leu Gln Glu Asp Arg Gly Asn Asp Ile Ser Pro Phe Ser Gly

```
                1               5                  10                  15
Asp Gly Gln Pro Phe Lys Asp
            20

<210> SEQ ID NO 6
<211> LENGTH: 23
<212> TYPE: PRT
<213> ORGANISM: Artificial Sequence
<220> FEATURE:
<223> OTHER INFORMATION: synthetic peptide

<400> SEQUENCE: 6

Thr Asp Leu Gln Glu Arg Trp Asp Asn Asp Ile Ser Pro Phe Ser Gly
  1               5                  10                  15

Asp Gly Gln Pro Phe Lys Asp
            20

<210> SEQ ID NO 7
<211> LENGTH: 23
<212> TYPE: PRT
<213> ORGANISM: Artificial Sequence
<220> FEATURE:
<223> OTHER INFORMATION: synthetic peptide

<400> SEQUENCE: 7

Thr Asp Leu Gln Glu Arg Gly Asp Asn Asp Met Ser Pro Phe Ser Gly
  1               5                  10                  15

Asp Gly Gln Pro Phe Lys Asp
            20

<210> SEQ ID NO 8
<211> LENGTH: 23
<212> TYPE: PRT
<213> ORGANISM: Artificial Sequence
<220> FEATURE:
<223> OTHER INFORMATION: synthetic peptide

<400> SEQUENCE: 8

Pro Asp Leu Gln Glu Arg Gly Asp Asn Asp Ile Ser Pro Phe Ser Gly
  1               5                  10                  15

Asp Gly Gln Pro Phe Lys Asp
            20

<210> SEQ ID NO 9
<211> LENGTH: 23
<212> TYPE: PRT
<213> ORGANISM: Artificial Sequence
<220> FEATURE:
<223> OTHER INFORMATION: synthetic peptide

<400> SEQUENCE: 9

Pro Asp Leu Gln Gly Arg Gly Asp Asn Asp Leu Ser Pro Phe Ser Gly
  1               5                  10                  15

Asp Gly Pro Pro Phe Lys Asp
            20

<210> SEQ ID NO 10
<211> LENGTH: 23
<212> TYPE: PRT
<213> ORGANISM: Artificial Sequence
<220> FEATURE:
<223> OTHER INFORMATION: synthetic peptide

<400> SEQUENCE: 10
```

```
Pro Asp Leu Leu Val Arg Gly Asp Asn Asp Val Pro Pro Phe Ser Gly
 1           5                  10                  15

Asp Gly Gln His Phe Met His
            20
```